United States Patent [19]

Pfirmann et al.

[11] Patent Number: 5,723,658
[45] Date of Patent: Mar. 3, 1998

[54] PROCESS FOR THE PREPARATION OF SALTS OF SUBSTITUTED OR UNSUBSTITUTED PHTHALIC ACIDS

[75] Inventors: Ralf Pfirmann, Griesheim; Theodor Papenfuhs, Frankfurt, both of Germany

[73] Assignee: Hoechst Aktiengesellschaft, Germany

[21] Appl. No.: 641,757

[22] Filed: May 2, 1996

[30] Foreign Application Priority Data

May 2, 1995 [DE] Germany .................. 195 15 986.1

[51] Int. Cl.$^6$ .................. C07C 63/16; C07C 63/17
[52] U.S. Cl. .................. 562/480; 562/483; 562/493; 564/149
[58] Field of Search .................. 562/493, 480, 562/483; 564/149

[56] References Cited

U.S. PATENT DOCUMENTS

| | | |
|---|---|---|
| 4,769,493 | 9/1988 | Ito et al. |
| 5,274,115 | 12/1993 | Papenfuhs et al. |
| 5,384,413 | 1/1995 | Pfirmann et al. |

FOREIGN PATENT DOCUMENTS

| | | |
|---|---|---|
| 0259663 | 3/1988 | European Pat. Off. |
| 0510491 | 10/1992 | European Pat. Off. |
| 0578165 | 1/1994 | European Pat. Off. |

*Primary Examiner*—C. Warren Ivy
*Assistant Examiner*—Jean F. Vollano
*Attorney, Agent, or Firm*—Connolly and Hutz

[57] ABSTRACT

The present invention relates to a process for the preparation of salts of substituted or unsubstituted phthalic acids, by reacting a compound of the formula

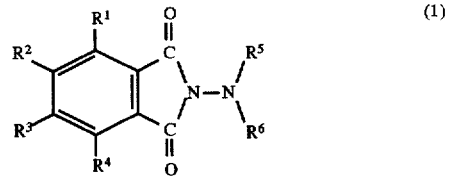

(1)

in which $R^1$, $R^2$, $R^3$ and $R^4$ are identical or different and are H, F, Cl, Br, $CF_3$, OH, an alkoxy or alkyl radical in each case having 1 to 4 carbon atoms, or a radical —$NR^7R^8$, in which $R^7$ and $R^8$ are identical or different and are H, an alkyl radical having 1 to 4 carbon atoms, or a phenyl radical, $R^5$ and $R^6$ are identical or different and are H, a —CO— alkyl group having 1 to 6 carbon atoms in the alkyl radical, or a benzoyl group, or $R^5$ and $R^6$ together form a radical of the formula

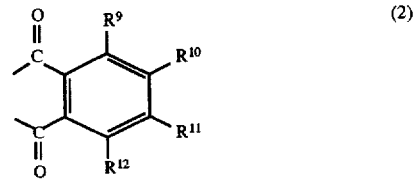

(2)

in which $R^9$, $R^{10}$, $R^{11}$ and $R^{12}$ are identical or different and are H, F, Cl, Br, $CF_3$, OH, an alkoxy or alkyl radical in each case having 1 to 4 carbon atoms, or a radical —$NR^7R^8$, in which $R^7$ and $R^8$ are identical or different and are H, an alkyl radical having 1 to 4 carbon atoms, or a phenyl radical, with water, a water-soluble base, and an oxidizing agent at a temperature of −10° to 150° C. in the presence or absence of a water-insoluble solvent inert under the reaction conditions.

23 Claims, No Drawings

PROCESS FOR THE PREPARATION OF SALTS OF SUBSTITUTED OR UNSUBSTITUTED PHTHALIC ACIDS

DESCRIPTION

The present invention relates to a process for the preparation of salts of substituted or unsubstituted, in particular substituted, phthalic acids.

Within the group of substituted phthalic acids, halogenated phthalic acids, in particular chlorinated and fluorinated phthalic acids, are of great importance. The chlorinated phthalic acids serve as starting material for fluorinated phthalic acids, which are themselves important intermediates for the preparation of antibacterial compositions (German Offenlegungsschrift 33 18 145, EP 424 850, EP 271 275).

Tetrafluorophthalic acid serves, for example, as starting material for the preparation of polymers (JP 02/29406), but it may also be used for the preparation of photosensitive materials (JP 01/268662, JP 11955 (1986)) or of liquid crystals (EP 0 602 596, EP 0 602 549).

Various routes for the preparation of tetrafluorophthalic acid are described in the literature.

Tetrafluorophthalic acid can be prepared, for example, from tetrachlorophthaloyl chloride (G. G. Yakobsen et al., Zh. Obshsh. Khim. 36 (1966), 139; EP 0 140 482, GB 2 146 635), from tetrachloroanthranilic acid (S. Hayashi et al., Bull. Chem. Soc. Jap. 45 (1972), 2909), from 1,2,3,4-tetrafluorobenzene (L. J. Belf et al., Tetrahedron 23 (1967), 4719; Z. Naturforsch. 31B (1976), 1667), from tetrachlorophthalic anhydride (DE-A 3 810 093; EP 0 218 111) or from tetrachlorophthalodinitrile (GB 2 134 900) via steps some of which are complex and/or cannot be implemented industrially or only with difficulty. The same statement also applies to the preparation of tetrafluorophthalic acid from 1,2-dibromotetrafluorobenzene (C. Tamborski et al., J. Organometallic Chem. 10 (1967), 385) and the method described by P. Sartori et al. (Chem. Ber. 101 (1968), 2004), starting from octafluoronaphthalene. N-carbon-substituted tetrachlorophthalimides (EP 0 259 663) are likewise used. After fluorination, these can be reacted via in some cases unselective steps (JP 02/145 538) without intermediate isolation of the tetrafluorophthalic acid, but with isolation of one of its functional derivatives, to give 2,3,4,5-tetrafluorobenzoic acid, a precursor likewise important for the synthesis of antibacterial compositions. The functional derivatives isolated intermediately can be hydrolyzed to give tetrafluorophthalic acid.

Another process starts from N-substituted tetrafluorophthalimides which are converted to tetrafluorophthalic acid by acid hydrolysis (EP 0 578 165). This reaction can also be carried out without addition of acid catalysts. A reason for this is apparently that the tetrafluorophthalic acid eliminated during the hydrolysis causes the reaction to proceed as an autocatalytic process. A disadvantage of this process is that, on the one hand, it is restricted to the conversion of tetrafluorophthalimides and only makes tetrafluorophthalic acid available, and that, on the other hand, the reaction is carried out in the acidic medium, which leads to considerable corrosion problems.

The preparation of N-substituted tetrafluorophthalimides is described in EP 510 491. Tetrachlorophthalic anhydride is reacted with at least the equimolar amount, expediently with an excess, of hydrazine or an N,N-disubstituted hydrazine in aqueous alcoholic medium, in glacial acetic acid, in sulfuric acid or oleum at temperatures of 100° to 220° C. to give the corresponding N'-substituted N-aminotetrachlorophthalimide and then chlorine is replaced with fluorine (halex reaction). This procedure can generally be applied to the preparation of N-substituted phthalimides by reacting the corresponding substituted or unsubstituted phthalic acids with hydrazine or a correspondingly substituted hydrazine and, if desired, carrying out a chlorine-fluorine exchange.

The object underlying the present invention is to provide a simple process for the preparation of salts of substituted or unsubstituted phthalic acids, which can be implemented without great expenditure on equipment and makes salts of a multiplicity of phthalic acids available, from which the corresponding phthalic acids may be released by a simple acidification. The process is intended to deliver the desired products of value with high conversion rate and high selectivity and to cause as few problems as possible with respect to corrosion.

This object is achieved by a process for the preparation of salts of substituted or unsubstituted phthalic acids. It comprises reacting a compound of the formula

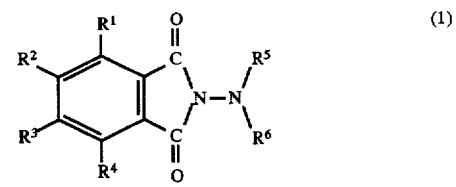

in which $R^1$, $R^2$, $R^3$ and $R^4$ are identical or different and are H, F, Cl, Br, $CF_3$, OH, an alkoxy or alkyl radical in each case having 1 to 4 carbon atoms, or a radical $—NR^7R^8$, in which $R^7$ and $R^8$ are identical or different and are H, an alkyl radical having 1 to 4 carbon atoms, or a phenyl radical, $R^5$ and $R^6$ are identical or different and are H, a —CO—alkyl group having 1 to 6 carbon atoms in the alkyl radical, or a benzoyl group, or $R^5$ and $R^6$ together form a radical of the formula

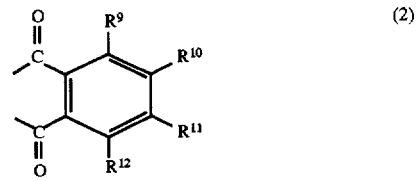

in which $R^9$, $R^{10}$, $R^{11}$ and $R^{12}$ are identical or different and are H, F, Cl, Br, CF3, OH, an alkoxy or alkyl radical in each case having 1 to 4 carbon atoms, or a radical $—NR^7R^8$, in which $R^7$ and $R^8$ are identical or different and are H, an alkyl radical having 1 to 4 carbon atoms, or a phenyl radical, with water, a water-soluble base and an oxidizing agent at a temperature of −10° to 150° C. in the presence or absence of a water-insoluble solvent inert under the reaction conditions.

The process of the invention has a plurality of advantages with respect to the prior art, in particular with respect to EP 0 578 165. It may be employed for the preparation of salts of a multiplicity of different phthalic acids and is not restricted to the use of N-substituted tetrafluorophthalimides. Problems with respect to corrosion, caused by acids or formation of acids, for example HF, do not occur, since the water-soluble base prevents the formation of free acid. This also avoids the corrosion problems occurring with the use of an acid catalyst, for example mineral acid. In comparison with the process of EP 0 578 165, the process of the invention may be carried out under yet milder conditions, in particular lower temperatures, without risk of corrosion and, furthermore, gives still higher yields. An additional advantage is the fact that the salts may be further processed in the form of their solution, as they arise as reaction product, without relatively great expenditure. It is not necessary here to isolate the corresponding substituted or unsubstituted phthalic acids. In addition, if desired, the corresponding phthalic acids may be prepared using the process of the invention in a very simple manner, that is by acidifying the aqueous solutions of phthalic acid salts.

The process of the invention may be handled flexibly, for example by employing, initially, relatively low temperatures and then relatively high temperatures, or by employing relatively high temperatures from the start, and, apart from the hydrolysis, also allowing an exchange reaction to proceed: for example halogen, in particular fluorine, for hydroxide. If an exchange of this type is to be prevented, the process is carried out at relatively low temperatures.

It is considered surprising that, under the conditions of the reaction, halogens, in particular fluorine, are not uncontrollably exchanged for hydroxyl groups, but that it is possible as desired to avoid this exchange or to carry it out specifically.

A compound of the formula (1) in which $R^1$, $R^2$, $R^3$ and $R^4$ are identical or different and are H, F, Cl, OH or an alkoxy radical having 1 to 4 carbon atoms, in particular F, OH or an alkoxy radical having 1 to 4 carbon atoms, can be used in the process highly successfully.

In the process, a compound of the formula (1) is preferably used in which $R^5$ and $R^6$ form a radical (2), $R^9$, $R^{10}$, $R^{11}$ and $R^{12}$ are identical or different and are H, F, Cl, OH or an alkoxyradical having 1 to 4 carbon atoms, in particular F, OH or an alkoxy radical having 1 to 4 carbon atoms.

Compounds of the formula (3) are of particular interest

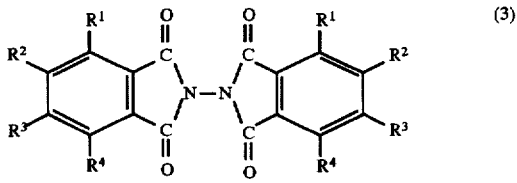

in which $R^1$, $R^2$, $R^3$ and $R^4$ have the meanings given above. 1 mol of these compounds gives in each case 2 mol of the corresponding phthalic salts. In addition, the formation of further byproducts originating from the hydrolysis is avoided.

Fluorinated compounds of the formula (1) are likewise of importance.

These compounds are N'-substituted N-aminofluorophthalimides which, in addition to fluorine, can also contain other substituents. They may be prepared in a comparatively simple manner, for example, starting from correspondingly substituted chlorophthalic anhydrides or correspondingly substituted chlorophthalic acids, by reaction with hydrazine sulfate or a correspondingly substituted hydrazine sulfate in sulfuric acid and subsequent chlorine-fluorine exchange.

Without making a claim as to completeness, suitable N'-substituted N-aminofluorophthalimides which may be mentioned are N'-diacylaminomonofluorophthaiimides, N'-diacylaminodifluorophthalimides, N-diacylaminotetrafluorophthalimides, 3,4,6-trifluorobisphthalimides, octafluorobisphthalimide, N'-dibenzoylaminomonofluorophthalimides, N'-dibenzoylaminodifluorophthalimides, N'-dibenzoylaminotetrafluorophthalimides, hexafluorobisphthalimides, tetrafluorobisphthalimides, in particular hexafluorobisphthalimide and octafluorobisphthalimide.

Particular interest is attached to the octafluorobisphthalimide

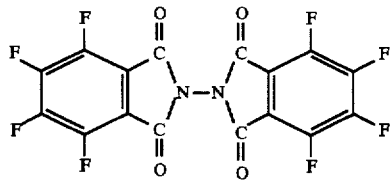

which is represented by the formula above.

This is because the process of the invention may be carried out particularly advantageously using octafluorobisphthalimide. In the hydrolysis of one mole of octafluorobisphthalimide, 2 mol of salts of tetrafluorophthalic acid are formed which, if appropriate, can be converted into tetrafluorophthalic acid or tetrafluorophthalic anhydride by acidification. This makes the reaction particularly simple and also leads to the avoidance of other byproducts originating from the hydrolysis.

To carry out the reaction, 2 to 3000, in particular 10 to 500, preferably 30 to 200, mol of water are added per mole of phthalic salts to be released.

If only the hydrolysis is to be carried out, comparatively small amounts of water are usually added, for example 2 to 10, in particular 2.2 to 6, mol of water per mole of phthalic acid to be released.

If, on the other hand, it is desired to prepare an aqueous solution of salts of the phthalic acids, as can be used for further processing, it is advisable to employ comparatively large amounts of water, for example 50 to 500, in particular 100 to 300, mol of water per mole of phthalic salts to be released.

It is thus generally advisable to use water at least in the stoichiometrically required amount or, advantageously, in an appropriately chosen excess. How large an excess of water is selected is a function, as described above, of the particular variant of the hydrolysis.

2 to 30, in particular 3 to 15, preferably 4 to 10, equivalents of the water-soluble base are usually used per mole of phthalic salts to be released.

Any base can be used for the reaction which is strong enough to induce the desired hydrolysis. Suitable water-soluble bases are alkali metal oxides, alkali metal hydroxides, alkaline earth metal oxides or alkaline earth metal hydroxides or mixtures of the same. Sodium hydroxide or potassium hydroxide are particularly suitable.

The reaction proceeds in a basic medium. It can be useful, during the hydrolysis, for the pH not to fall below a certain value, for example pH=10, in particular pH=11, preferably pH=12. If desired, the water-soluble base can be added in the amount in which it is consumed by the reaction taking place. In this manner, the reaction can be carried out specifically and can be monitored simply.

To carry out the process, an oxidizing agent is additionally required. A suitable oxidizing agent is any oxidant which ensures that hydrazine is oxidized to nitrogen under the conditions of the process. The oxidizing agent is used at I to 5 times, in particular 1.05 to 2 times, the amount required for the oxidation of hydrazine to nitrogen.

Usually, the oxidizing agent is used in at least the amount stoichiometrically required for the oxidation of hydrazine to nitrogen, or up to an excess of 2 to 30, in particular 3 to 10%, of the stoichiometrically required amount.

If the oxidizing agent is used in excess, it can be expedient, after completion of the reaction, to eliminate any oxidizing agent still present by addition of a reducing agent.

Usually, the oxidizing agent used is a halogen, a hypohalite, hydrogen peroxide, $NO_2$, $N_2O_4$, $N_2O_3$, $N_2O_5$, a nitrite or a mixture of the same. Substances can also be used from which the actual oxidizing agent is formed.

Highly suitable oxidizing agents are $Cl_2$, $Br_2$, $I_2$, $ClO^-$, $BrO^-$, $IO^-$ or mixtures of the same. The use of hypohalite-containing halogen bleaching liquors, in particular hypohalite-containing chlorine bleaching liquor, is particularly expedient. However, the hypohalite can be generated in situ by introducing halogen into the basic reaction medium.

When the water-soluble base and the oxidizing agent are being added, there is no restriction to any particular sequence. The water-soluble base and the oxidizing agent can be added simultaneously. It is also possible first to add the entire amount or a partial amount of the water-soluble base and then to add the oxidizing agent. However, the water-soluble base can be added first and the oxidizing agent can be metered in simultaneously or staggered in time during the addition of the base, or the oxidizing agent can be metered in after completion of the addition of the base.

As mentioned at the outset, the process of the invention is carried out at a temperature of −10 to 150, in particular −5 to 110, preferably 0° to 80° C.

The process may be handled flexibly, as already described above, by first allowing the actual hydrolysis to proceed at relatively low temperatures, for example at −10 to 60, in particular −5 to 50, preferably 0° to 40° C., and then allowing a further reaction, for example an exchange reaction, to proceed at relatively high temperatures, for example at 40 to 150, in particular 50 to 110, preferably 60° to 90° C. A suitable corresponding reaction is an exchange of halogen, in particular fluorine, for hydroxyl.

However, the hydrolysis alone, or the hydrolysis and the exchange reaction, can also be carried out from the start at comparatively high temperatures. The choice of the reaction temperatures depends to a certain extent also on the starting material. Highly reactive starting materials may be reacted even at relatively low temperatures, whereas less reactive starting materials require reaction at high temperatures. The type of exchange reaction also obviously influences the level of the reaction temperature. If the exchange reaction is the exchange of a relatively unreactive group or radical, relatively high temperatures will be employed.

The reaction is carried out in the presence or absence of a water-insoluble solvent inert under the reaction conditions. Suitable solvents are, without making a claim as to completeness, for example, toluene, o-xylene, m-xylene, p-xylene, mixtures of isomeric xylenes, mesitylene, ethylbenzene, chlorinated benzenes such as chlorobenzene, dichlorobenzene or chlorotoluene, chlorinated hydrocarbons such as chloroform or dichloromethane, ethers, in particular toluene, o-xylene, m-xylene, p-xylene, mixtures of isomeric xylenes, aromatics having two benzene rings, such as biphenyl, diphenylmethane or diphenyl ether, preferably o-xylene, m-xylene, p-xylene, mixtures of isomeric xylenes, diphenylmethane or mixtures of these solvents. It is also possible, in particular, to use commercial heat-transfer oils comprising alkylated benzenes and/or diphenyl ethers, which, for example, are commercially available under the name Dowtherm®, Diphyl® or Santotherm®.

It can likewise be expedient to carry out the process in the presence of small amounts of inert, polar aprotic solvents, as are present, for example, in the crude products of the N'-substituted N-amino-tetrafluorophthalimides obtained from the chlorine/fluorine exchange reaction. These additions can lead to a higher reaction rate, possibly because of their solubilizer characteristics. Thus crude products, as arise in the synthesis, for example in the chlorine/fluorine exchange, can also particularly advantageously be employed as starting material.

Suitable inert, polar aprotic solvents are, for example, sulfolane (tetramethylene sulfone), tetramethylene sulfoxide, dimethyl sulfoxide, dimethyl sulfone, diphenyl sulfoxlde, diphenyl sulfone or mixtures of the same. These solvents are, if appropriate, present in the reaction mixture used as starting material in amounts between about 0.1% and about 5%, preferably between about 0.2% and about 2%.

However, the addition of a solvent can generally be avoided.

If it is intended to prepare the corresponding substituted or unsubstituted phthalic acids, the reaction mixture arising is acidified, for example by addition of mineral acid, and the phthalic acid released is separated off, for example by filtration or extraction.

The examples below describe the invention in more detail without restricting it thereto.

EXPERIMENTAL SECTION

EXAMPLE 1

Preparation of tetrachlorophthalic acid 30 g (0.1 mol) of N-aminotetrachlorophthalimide are introduced into 150 g of water and 32 g (0.8 mol) of sodium hydroxide. Chlorine is then passed in for 1 hour with stirring at 20° C. The amount of chlorine metered in is 17.2 g (0.243 mol).

A fine suspension forms, this is stirred for a further 5 hours at 30° C., excess chlorine or hypochlorite is destroyed by addition of 0.3 g of sodium dithionite, and sulfurlc acid is added to a pH of I with cooling to 2° C. (ice bath). The then more easily stirrable suspension is filtered with suction and the filter cake is washed twice, each time with 50 g of water.

After drying, 27.7 g (91% of theory) of tetrachlorophthalic acid are obtained as a light-yellowish powder.

EXAMPLE 2

Preparation of a mixture of tetrachlorophthalic acid and benzoic acid

The procedure as specified in Example 1 is followed but, instead of N-aminotetrachlorophthalimide, 41 g (0.1 mol) of approximately 98% pure N'-benzoyl-N-aminotetrachlorophthalimide and 36 9 (0.9 mol) of sodium hydroxide are used.

The amount of chlorine metered in is 18.0 g.

The procedure as specified in Example 1 is followed further, excess chlorine or hypochlorite is destroyed, the mixture is acidified and filtered and the filter product is dried. 39 g of a light-yellowish mixture comprising tetrachlorophthalic acid and benzoic acid are obtained.

EXAMPLE 3

Preparation of 3,5,6-trichlorophthalic acid 50 g (purity 85 to 90%) of 3,3',5,5',6,6'-hexachlorobisphthalimide are introduced at 30° C. over the course of 1 hour into a bleaching liquor prepared from 21.3 g (0.3 mol) of chlorine, 40 g (1 mol) of sodium hydroxide and 150 g of water. The mixture is further stirred (5.25 hours) until HPLC indicates complete conversion. Excess chlorine or hypochlorite is destroyed by addition of 0.5 g of sodium sulfite at 20° C. and the mixture is acidified with technical grade hydrochloric acid (30% strength) to a pH of 1.

The suspension is filtered with suction, and the filter cake is washed with 100 g of water.

After drying, 22.1 g (82% of theory) of 3,5,6-trichlorophthalic acid are obtained as a light-gray, fine powder.

EXAMPLE 4

Preparation of 3,5,6-trifluorophthalic acid 28 g (purity 85 to 90%) of a crude brown 3,3',5,5',6,6'-hexafluorobisphthalimide, which was prepared from hexachlorobisphthalimide by chlorine-fluorine exchange, are introduced at 10° C. into a mixture comprising 80 g of water and 28 g of (85% pure) potassium hydroxide. Then, a total of 32 g (0.2 mol) of bromine are added dropwise with stirring at 20° C. and the mixture is further stirred (30 minutes) at this temperature until HPLC indicates complete conversion. Excess bromine or hypobromite is destroyed by addition of 3 g of sodium dithionite, and the mixture is acidified to pH 1 and continuously extracted (5 hours) with methyl tert-butyl ether. The resulting organic phase is dried over $MgSO_4$ and the solvent is removed in vacuo.

13 g (purity approximately 86%) of a brown oil are obtained, corresponding to a yield of 80 to 85%, based on hexafluorobisphthalimide used in pure form.

EXAMPLE 5

Preparation of the potassium salt of 4-hydroxy-3,5,6-trifluorophthalic acid 85.4 g of water and 43.6 g (0.66 mol) of potassium hydroxide (85% pure) are taken and 25.3 g (0.05 mol) of 86.3% pure octafluorobisphthalimide are introduced with stirring at 5° C. over 2 hours. Then, 7.8 g (0.11 mol) of chlorine are passed into the mixture at 5° C. (cooling bath) with stirring over 30 minutes, the suspension clarifying and transforming into a solution. After 1 hour of further stirring, HPLC indicates complete conversion, but excess chlorine or hypochlorite is still present. The cooling bath is removed and the temperature allowed to increase to 20° C. in the course of 3 hours. To remove excess chlorine or hypochlorite, 1.8 g of sodium sulfite and then 8.7 g of potassium hydroxide are added, and the mixture is heated at 70° C. with stirring for 5 hours.

187 g of a clear solution are obtained which contains the potassium salt equivalent to an amount of 14.11 g (0.0597 mol) of 4-hydroxy-3,5,6-trifluorophthalic acid (yield: 59.7% of theory).

This aqueous solution can be further processed directly; isolation of the product as salt or free acid is not necessary.

EXAMPLE 6

Preparation of the potassium salt of 4-hydroxy-3,5,6-trifluorophthalic acid 85.4 g of water and 43.6 g (0.66 mol) of potassium hydroxide (85% pure) are taken and 25.3 g (0.05 mol) of 86.3% pure octafluorobisphthalimide are introduced with stirring at 10° to 15° C. over 2 hours. The mixture is then admixed with 0.11 mol of bromine in the form of a bromine bleaching liquor prepared from 17.6 g (0.11 mol) of bromine, 21.8 g of 85% pure KOB and 47.7 g of water, at 15° to 20° C. over 2 hours.

The resulting brown solution is further stirred for 1 hour and then admixed with 0.7 g of sodium dithionite. The mixture is then heated at 70° C. for 6.75 hours and 255.7 g of a clear brown aqueous solution are obtained, which contains the potassium salt equivalent to an amount of 21.6 g of 4-hydroxy-3,5,6-trifluorphthalic acid (yield: 91.5% of theory).

This aqueous solution can be further processed directly; isolation of the product as salt or free acid is not necessary.

Similar results are obtained if at the start of the reaction 6.5 g of potassium bromide are placed in the water and potassium hydroxide and, instead of bromine bleaching liquor, a chlorine bleaching liquor prepared from 2.46 l of chlorine gas, 21.8 g of potassium hydroxide and 42.7 g of water is used; the procedure is otherwise performed as described above.

EXAMPLE 7

Preparation of tetrafluorophthalic acid 85.4 g of water and 43.6 g (0.66 mol) of 85% pure potassium hydroxide and 30 g of xylene are taken and 25.3 g of 86.3% pure octafluorobisphthalimide are introduced at 0° to 5° C. over 2 hours with stirring. A thick light-brown suspension is obtained, and 27.6 g (0.11 mol) of iodine are added over 30 minutes at 5° to 7° C. and, simultaneously, a further 20 g of water are added dropwise. At the end, a light-brown clear solution is obtained with a supernatant organic phase. The solution is stirred for a further 16 hours, 3.5 g of sodium sulfite are added and the organic phase, which is discarded, is separated off. The aqueous phase is adjusted to pH=1 with 96% strength sulfuric acid and extracted with methyl tert-butyl ether.

The organic phase is dried and the solvent removed under vacuum.

28.0 g of a brown, slowly crystallizing residue are obtained which, measured by means of calibrated HPLC, contains 16.2 g (0.068 mol) of tetrafluorophthalic acid (yield 68% of theory).

Comparison example

Reaction without addition of an oxidizing agent 85.4 g of water, 43.6 g of 85% pure potassium hydroxide, 30 g of diphenyl ether and 5 g of xylene are taken and 25.3 g of 86.3% pure octafluorobisphthalimide (divided into 8 equal portions) are added at 15° C. over 2 hours with stirring. The mixture is further stirred for 2 hours.

Analysis (HPLC; $^1$H-NMR) shows that only one product with a single ring opening has formed, and the conversion to unidentified secondary products is <2%. The potassium salt of tetrafluorophthalic acid or the free acid can not be detected.

The mixture is then heated to 23° C. and stirred at this temperature for 18.75 hours.

Even after this time, the mixture is still unchanged. Subsequently, the temperature is increased to 40° to 45° C. with stirring for 2.25 hours. Analysis shows that still only one product with a single ring opening has formed, and the conversion to unidentified secondary products is about 5%. The potassium salt of tetrafluorophthalic acid or the free acid can not be detected.

Increasing the temperature over 3 hours to 60° C. leads to a product in which neither the potassium salt of tetrafluorophthalic acid or the free acid nor the potassium salt of 4-hydroxy-3,5,6-trifluorophthalic acid or the free acid can be detected. Conversion does take place (about 40%), which leads in part to intermediates which do not react further, but can still be reacted—as the control experiment proves—to give the potassium salt of 4-hydroxy-3,5,6-trifluorophthalic acid.

Control experiment (subsequent to the comparison example)

Continuation of the comparison example with addition of an oxidizing agent

The reaction mixture obtained in the comparison example is admixed with 68.4 g of a 6.7% strength chlorine bleaching liquor and 21 g of water over 2.5 hours at 15° C. with stirring. As soon as the addition is ended, starting material still present, that is octafluorobisphthalimide, has been converted completely to the potassium salt of tetrafluorophthalic acid.

The mixture is further stirred for 20 hours at this temperature in order to convert as far as possible the intermediates originating from the unusual course of reaction, and then the mixture is reacted over 5 hours at 70° C. to give the potassium salt of 4-hydroxy-3,5,6-trifluorophthalic acid.

The reaction mixture contains the potassium salt of 4-hydroxy-3,5,6-trifluorophthalic acid in a yield of still 79.5% of theory (measured by HPLC with an internal standard).

EXAMPLE 8

Preparation of the potassium salt of 4-hydroxy-3,5,6-trifluorophthalic acid 247.6 g of a 6.7% strength chlorine bleaching liquor, 17.2 g of water, 8.6 g of potassium hydroxide and 30 g of diphenyl ether are taken and 25.3 g (0.05 mol) of octafluorobisphthalimide are introduced at 13° to 21° C. over 1.75 hours with stirring. The mixture is stirred for a further 3.5 hours, 5 g of xylene being added after 3 hours. A mixture containing two phases is produced. The aqueous phase is separated off and heated for 2 hours with stirring at 70° C. The aqueous solution obtained after cooling contains the potassium salt equivalent to an amount of 13.5 g of 4-hydroxy-3,5,6-trifluorophthalic acid (yield 57.2% of theory).

EXAMPLE 9

Preparation of the potassium salt of 4-hydroxy-3,5,6-trifluorophthalic acid 133.1 g of water, 65.4 g (0.66 mol) of potassium hydroxide, 30 g of dichlorotoluene and 10 g of a mixture of various aliphatic trialkylamines having 6 to 14 carbon atoms in the alkyl radical (Hostarex 327; commercial product from Hoechst AG) are taken and 25.3 g (0.05 mol) of 86.3% pure octafluorobisphthalimide are introduced at 5° to 10° C. over 1 hour. Then, 17.6 g.(0.11 mol) of bromine are added with vigorous stirring over 5 hours at 10° to 12° C., and the mixture is further stirred for one hour and then admixed with 0.3 g of sodium dithionite. The mixture is then heated for 3 hours with stirring at 80° C. and a mixture composed of 2 phases is obtained. The lower phase corresponds to 279.9 g of a clear brown aqueous phase which contains the potassium salt equivalent to an amount of 20.0 g of 4-hydroxy-3,5,6-trifluorophthalic acid (yield: 84.7% of theory).

The mixture comprising 2 phases can be further processed directly without phase separation and without isolation of a product.

We claim:

1. A process for the preparation of salts of substituted or unsubstituted phthalic acids, which comprises reacting a compound of the formula

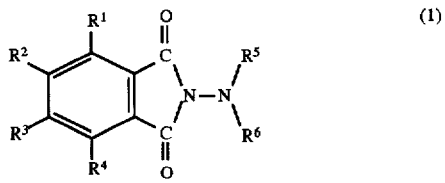

(1)

in which $R^1$, $R^2$, $R^3$ and $R^4$ are identical or different and are H, F, Cl, Br, $CF_3$, OH, an alkoxy or alkyl radical in each case having 1 to 4 carbon atoms, or a radical $—NR^7R^8$, in which $R^7$ and $R^8$ are identical or different and are H, an alkyl radical having 1 to 4 carbon atoms, or a phenyl radical, $R^5$ and $R^6$ are identical or different and are H, a $—CO—$alkyl group having 1 to 6 carbon atoms in the alkyl radical, or a benzoyl group, or $R^5$ and $R^6$ together form a radical of the formula

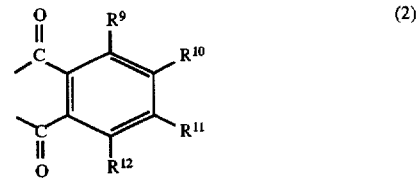

(2)

in which $R^9$, $R^{10}$, $R^{11}$ and $R^{12}$ are identical or different and are E, F, Cl, Br, $CF_3$, OH, an alkoxy or alkyl radical in each case having 1 to 4 carbon atoms, or a radical $—NR^7R^8$, in which $R^7$ and $R^8$ are identical or different and are H, an alkyl radical having 1 to 4 carbon atoms, or a phenyl radical, with water, a water-soluble base and an oxidizing agent at a temperature of $-10°$ to $150°$ C. in the presence or absence of a water-insoluble solvent inert under the reaction conditions.

2. The process as claimed in claim 1, wherein a compound of the formula (1) is used in which $R^1$, $R^2$, $R^3$ and $R^4$ are identical or different and are E, F, Cl, OH or an alkoxy radical having 1 to 4 carbon atoms.

3. The process as claimed in claim 1, wherein a compound of the formula (1) is used in which $R^1$, $R^2$, $R^3$ and $R^4$ are identical or different and are F, OH or an alkoxy radical having 1 to 4 carbon atoms.

4. The process as claimed in claim 1 wherein a compound of the formula (1) is used in which $R^5$ and $R^6$ form a radical (2), $R^9$, $R^{10}$, $R^{11}$ and $R^{12}$ are identical or different and are H, F, Cl, OH or an alkoxy radical having 1 to 4 carbon atoms.

5. The process as claimed in claim 1, wherein a compound of the formula (1) is used in which $R^5$ and $R^6$ form a radical (2), $R^9$, $R^{10}$, $R^{11}$ and $R^{12}$ are identical or different and are F, OH or an alkoxy radical having 1 to 4 carbon atoms.

6. The process as claimed in claim 1 wherein a compound of the formula (3)

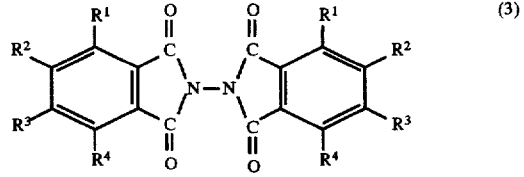

(3)

in which $R^1$, $R^2$, $R^3$ and $R^4$ have the meanings given above is used.

7. The process as claimed in claim 1, wherein octafluorobisphthalimide

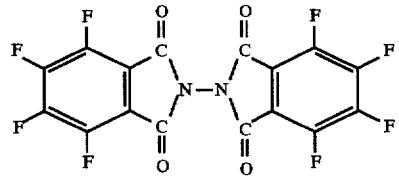

is used as the compound of formula (i).

8. The process as claimed in claim 1, wherein 2 to 3000 mol of water are used per mole of phthalic salts to be released.

9. The process as claimed in claim 1, wherein 2 to 30 equivalents of the water-soluble base are used per mole of phthalic salts to be released.

10. The process as claimed in claim 1, wherein the water-soluble base used is an alkali metal oxide, alkali metal hydroxide, alkaline earth metal oxide or alkaline earth metal hydroxide or a mixture of the same.

11. The process as claimed in claim 1, wherein the water-soluble base used is sodium hydroxide or potassium hydroxide.

12. The process as claimed in claim 1 wherein the oxidizing agent is added at 1 to 5 times the amount which is required for the oxidation of hydrazine to nitrogen.

13. The process as claimed in claim 1 wherein the oxidizing agent is added at 1.05 to 2 times the amount which is required for the oxidation of hydrazine to nitrogen.

14. The process as claimed in claim 1, wherein the oxidizing agent used is a halogen, a hypohalite, hydrogen peroxide, $NO_2$, $N_2O_4$, $N_2O_3$, $N_2O_5$, a nitrite or a mixture of the same.

15. The process as claimed in claim 1 wherein the oxidizing agent used is $Cl_2$, $Br_2$, $I_2$, $ClO^-$, $BrO^-$, $IO^-$ or mixtures of the same.

16. The process as claimed in claim 1, wherein the water-soluble base and the oxidizing agent are introduced simultaneously.

17. The process as claimed in claim 1 wherein the water-soluble base is first added and the oxidizing agent is added during the addition of the base or subsequent to the addition of the base.

18. The process as claimed in claim 1, wherein the reaction is carried out at $-5°$ to $110°$ C.

19. The process as claimed in claim 1, wherein 10 to 500 mol of water are used per mole of phthalic salts to be released.

20. The process as claimed in claim 1, wherein 30 to 200 mol of water are used per mole of phthalic salts to be released.

21. The process as claimed in claim 1, wherein 3 to 15 equivalents of the water-soluble base are used per mole of phthalic salts to be released.

22. The process as claimed in claim 1, wherein 4 to 10 equivalents of the water-soluble base are used per mole of phthalic salts to be released.

23. The process as claimed in claim 1, wherein the reaction is carried out at $0°$ to $90°$ C.

* * * * *